US010481116B2

United States Patent
Franzini et al.

(10) Patent No.: US 10,481,116 B2
(45) Date of Patent: Nov. 19, 2019

(54) HIGH RESOLUTION INSPECTION DEVICE FOR CASTING DEFECTS USING IR IMAGING

(71) Applicant: BAE Systems Information and Electronic Systems Integration Inc., Nashua, NH (US)

(72) Inventors: John R. Franzini, Hollis, NH (US); Mark B. Lyles, Exeter, RI (US); Robert H. Murphy, Lancaster, MA (US)

(73) Assignees: BAE Systems Information and Electronic Systems Integratlon Inc., Nashua, NH (US); Mark B. Lyles, Exeter, RI (US)

( * ) Notice: Subject to any disclaimer, the term of this patent is extended or adjusted under 35 U.S.C. 154(b) by 227 days.

(21) Appl. No.: 15/522,823

(22) PCT Filed: Aug. 7, 2015

(86) PCT No.: PCT/US2015/044195
§ 371 (c)(1),
(2) Date: Apr. 28, 2017

(87) PCT Pub. No.: WO2016/069085
PCT Pub. Date: May 6, 2016

(65) Prior Publication Data
US 2017/0328849 A1    Nov. 16, 2017

Related U.S. Application Data

(60) Provisional application No. 62/072,573, filed on Oct. 30, 2014.

(51) Int. Cl.
*G01N 25/72* (2006.01)
*H04N 5/44* (2011.01)
*G01J 5/00* (2006.01)

(52) U.S. Cl.
CPC ........... *G01N 25/72* (2013.01); *H04N 5/4403* (2013.01); *G01J 2005/0077* (2013.01); *H04N 2005/4426* (2013.01)

(58) Field of Classification Search
CPC .. G01J 5/025; G01J 2005/0077; G01J 5/0003; G01J 2005/0081;
(Continued)

(56) References Cited

U.S. PATENT DOCUMENTS 3,808,439 A * 4/1974 Renius .................... G01N 25/72
250/334
4,363,104 A * 12/1982 Nussmeier .......... G06F 15/8015
348/625
(Continued)

OTHER PUBLICATIONS

International Search Report, PCT/US2015/044195, dated Jan. 22, 2016, 12 pages.
EP Search Report, EP15854546.7, dated May 29, 2018, 9 pages.

*Primary Examiner* — Gail Kaplan Verbitsky
(74) *Attorney, Agent, or Firm* — Scott J. Asmus

(57) ABSTRACT

A nondestructive system and method for high resolution thermal imaging in metal casting applications is provided to detect defects and starts with the article under test being subjected to a thermal gradient, followed by infrared images taken thereof. The creation of the thermal gradient results in any defects reacting differently to the thermal gradient application to accentuate the defect in the infrared image. The apparatus for conducting the tests in one embodiment includes a single channel sensor, remote cable, and a laptop controller with real time image processing software. This hardware provides high resolution, real-time viewable infrared (IR) images with a variable focus distance adjustable from six inches to infinity. The apparatus enables crisp, clear imagery of various metal casting defects.

11 Claims, 3 Drawing Sheets

(58) Field of Classification Search
CPC ............. G01J 2005/0085; G01J 5/0088; G01J 5/0066; G01J 5/0862; H01L 21/67248; H01L 21/67115; H01L 27/14669; G01N 25/72
USPC ........... 374/4, 5, 57, 121, 137, 112; 702/135
See application file for complete search history.

(56) References Cited

U.S. PATENT DOCUMENTS

| | | | | |
|---|---|---|---|---|
| 4,773,766 A * | 9/1988 | Nagasaka | ............. | G01D 9/005 250/340 |
| 4,996,426 A * | 2/1991 | Cielo | ............. | G01N 25/72 250/330 |
| 5,654,977 A | 8/1997 | Morris | | |
| 7,083,327 B1 * | 8/2006 | Shepard | ............. | G01N 25/72 374/124 |
| 7,999,841 B1 * | 8/2011 | Stevens | ............. | H04N 5/2259 348/218.1 |
| 8,581,975 B2 * | 11/2013 | Benzerrouk | ............. | G06T 7/0004 348/125 |
| 8,759,770 B1 * | 6/2014 | Woods | ............. | G01N 25/72 250/338.1 |
| 9,897,561 B2 * | 2/2018 | Isakov | ............. | G01N 25/72 |
| 2005/0156111 A1 * | 7/2005 | Racca | ............. | G01M 3/38 250/338.5 |
| 2006/0191622 A1 | 8/2006 | Ritter et al. | | |
| 2006/0291716 A1 | 12/2006 | Vaidyanathan | | |
| 2007/0120058 A1 | 5/2007 | Blackwell et al. | | |
| 2009/0114124 A1 | 5/2009 | Baldi et al. | | |
| 2012/0194711 A1 * | 8/2012 | Nikittin | ............. | H04N 5/33 348/241 |
| 2012/0286161 A1 | 11/2012 | Raieszadeh et al. | | |
| 2012/0327971 A1 * | 12/2012 | Goda | ............. | G01J 5/004 374/140 |
| 2013/0099123 A1 | 4/2013 | De Amicis et al. | | |
| 2014/0022380 A1 | 1/2014 | Nissen et al. | | |
| 2015/0163478 A1 * | 6/2015 | Geiss | ............. | H04N 13/243 348/47 |
| 2016/0287088 A1 * | 10/2016 | Case | ............. | A61B 5/015 |
| 2016/0317039 A1 * | 11/2016 | Franzini | ............. | A61B 5/7203 |
| 2017/0302864 A1 * | 10/2017 | Southerland | ............. | G01J 5/025 |

* cited by examiner

HIGH RESOLUTION INSPECTION DEVICE FOR CASTING DEFECTS USING IR IMAGING

STATEMENT OF GOVERNMENT INTEREST

This invention was made with United States Government assistance under Contract No. H94003-04-D-0002/0105 awarded by the Department of the Navy. The United States Government has certain rights in this invention.

CROSS-REFERENCE TO RELATED APPLICATIONS

This Application claims rights under 35 USC § 119(e) from U.S. Provisional Application Ser. No. 62/072,573 filed Oct. 30, 2014, the contents of which are incorporated herein by reference. This application is related to U.S. Application entitled "High Definition Thermal Imaging for Medical Applications" (U.S. application Ser. No. 15/109,140) filed on even date herewith, the contents of which are incorporated hereby by reference.

FIELD OF INVENTION

The present invention relates to high resolution thermal imaging using IR sensors combined with Real Time Image Processing algorithms. More particularly, the invention relates to the use of such thermal imaging in inspecting metal castings for defects.

BACKGROUND OF THE INVENTION

Typically, metal castings are inspected according to SAE AMS 2175. This specification establishes nondestructive test methods, sampling frequency and acceptance criteria. The two most common methods for metal casting inspection referenced in AMS 2175 are Magnetic Particle Inspection (MPI) and Radiographic Inspection (X-Ray).

Magnetic Particle Inspection (MPI)

Magnetic Particle Inspection is a non-destructive testing process for detecting surface and slightly subsurface discontinuities in iron, nickel, cobalt and ferromagnetic alloys. The method puts a magnetic field into the part. The unit under test (UUT) can be magnetized by either passing an electric current through the test object or when a magnetic field is applied from an outside source. A magnetic flux material is then applied over the UUT.

The presence of a surface or subsurface discontinuity in the material allows the magnetic flux to leak, since air cannot support as much magnetic field per unit volume as metals. Ferrous iron particles are then applied to the part. If an area of flux leakage is present, the particles will be attracted to this area and form what is known as an indication.

Cracks which would normally have been invisible are detectable due to the magnetic particles clustering at the crack openings. However, some drawbacks of Magnetic Particle Inspection include being restricted to ferromagnetic materials, and being a relatively messy process. Additionally, magnetic field strength is sometimes in question and the process cannot be used for painted castings. Moreover, interpretation requires skilled personnel and is considered a skilled task. Finally, the process requires a ventilated work area.

Radiographic Inspection (X-Ray)

Radiographic Testing is a nondestructive testing method for inspecting materials for hidden flaws by using the ability of short wavelength electromagnetic radiation to penetrate various materials.

Either an X-ray machine or a radioactive source is used as the source of photon generation to penetrate materials. Since the amount of radiation emerging from the opposite side of the material can be detected and measured, variations in this amount or intensity of radiation are used to determine thickness or composition of material. Some drawbacks of Radiographic Inspection include safety hazards, expense, slow reaction times, highly directional results, and interpretation requiring skilled personnel and constituting a skilled task. Moreover, depth of discontinuity is not indicated.

An improved means is needed for high resolution imaging of metal castings.

SUMMARY OF THE INVENTION

Embodiments of the present disclosure provide a device and method for high definition thermal imaging and close focus viewing of 6 inches to an infinite distance in metal casting inspection applications. Briefly described, in architecture, one embodiment of the device, among others, can be implemented as follows. The device has a single channel, uncooled thermal sensor in a camera, wherein the sensor has low noise characteristics. A remote cable is attached to the camera and connected to a laptop controller with enhanced real time image processing software.

The present disclosure can also be viewed as providing methods of nondestructive testing of an article for defects. In this regard, one embodiment of such a method, among others, can be broadly summarized by the following steps: subjecting the article to a thermal gradient; and providing an infrared image of the article during thermal gradient application.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

These and other features of the Subject Invention will be better understood in connection with the Detailed Description in conjunction with the Drawings of which.

DETAILED DESCRIPTION

Defects in metal castings can be detected through the utilization of infrared imagery and causing the casting to be subjected to a thermal gradient. Because of the existence of the thermal gradient, the defect absorbs heat differently compared to casting material to either side. This defect shows up as a distinct thermal trace on the IR image and therefore constitutes a convenient nondestructive method of finding defects in castings or other materials. In one embodiment, the casting is heated above ambient temperature to for instance 100° F. and is allowed to cool. During the cool down the thermal gradient is absorbed differently at the flaw or defect in the casting so that it becomes highly visible in the infrared image as the device cools and before it reaches thermal equilibrium.

Alternatively, one could cool down the casting, and then allow it to rise to ambient room temperature. The thermal trace, which is the result of the thermal gradient when the casting rises to ambient temperature, is also highly visible as the cooled casting heats up to ambient temperature.

In this way the nondestructive testing can be performed by inexperienced personnel and can even detect the defects in painted articles or castings.

In one embodiment, the present invention involves an apparatus for high resolution single channel thermal imaging of metal castings, and includes some or all of the following: a highly sensitive thermal imaging device or focal plane array (FPA), a remote cable and laptop controller with real time image processing software. It provides a single viewable IR channel with a variable focus distance which can be optimized at any distance from six inches to infinity. The present invention enables high quality vision in the thermal band for detection of casting defects within the field of view (FOV) from very close to distant objects and scenes. The system coupled with a created thermal gradient accentuates thermal representation of a defect as the article under test undergoes the thermal gradient.

In summary, a nondestructive system and method for high resolution thermal imaging in metal casting applications is provided to detect defects and starts with the article under test being subjected to a thermal gradient, followed by infrared images taken thereof. The creation of the thermal gradient results in any defects reacting differently to the thermal gradient application to accentuate the defect in the infrared image. The apparatus for conducting the tests in one embodiment includes a single channel sensor, remote cable, and a laptop controller with real time image processing software. This hardware provides high resolution, real-time viewable infrared (IR) images with a variable focus distance adjustable from six inches to infinity, with the apparatus enabling crisp, clear imagery of various metal casting defects.

Figure 1:
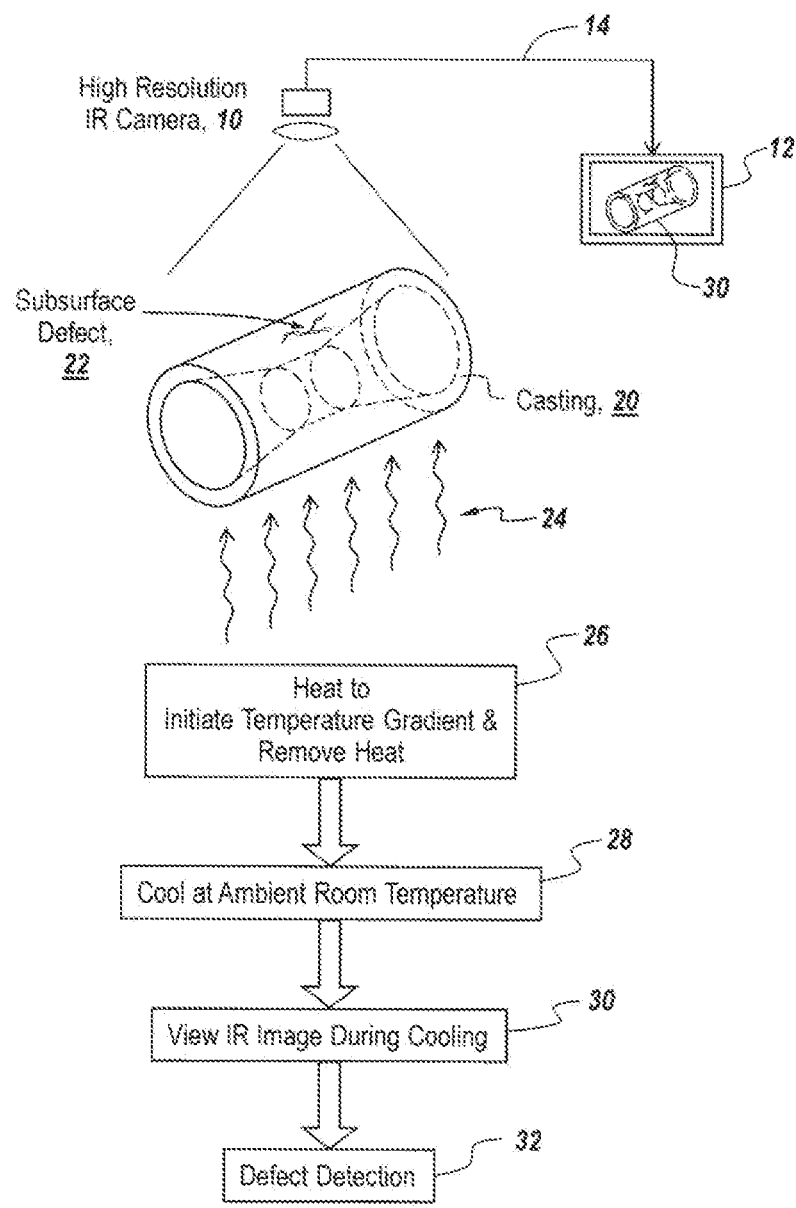
FIG. 1 is a diagrammatic representation of the process by which subsurface defects in a casting can be detected utilizing a high-resolution infrared camera coupled with providing a thermal gradient at the subsurface defect.

FIG. 1 is a diagrammatic representation of the process by which subsurface defects in a casting can be detected utilizing a high-resolution infrared camera coupled with providing a thermal gradient at the subsurface defect. In one embodiment, it consists of a 12 micron uncooled, low noise microbolometer focal plane array IR camera 10 coupled to a controller and a computer with the computer screen 12. The IR camera 10 is coupled to computer 12 via an HDMI signal cable 14. The IR camera 10 is powered up using the HDMI cable 14 and has no user controls or interfaces, greatly simplifying the user interface. A manual focus adjustment is provided at the objective lens of the camera for coarse adjustment. Due to the highly sensitive IR sensor in the camera and at 1-2 ft. of working distance, the system has an increased depth of field of greater than 6 inches, eliminating the need for autofocus motor controllers and associated complex control algorithms. The elimination of an autofocus motor controller is a major breakthrough and makes the unit smaller, lighter, more reliable and less expensive.

Figure 3:
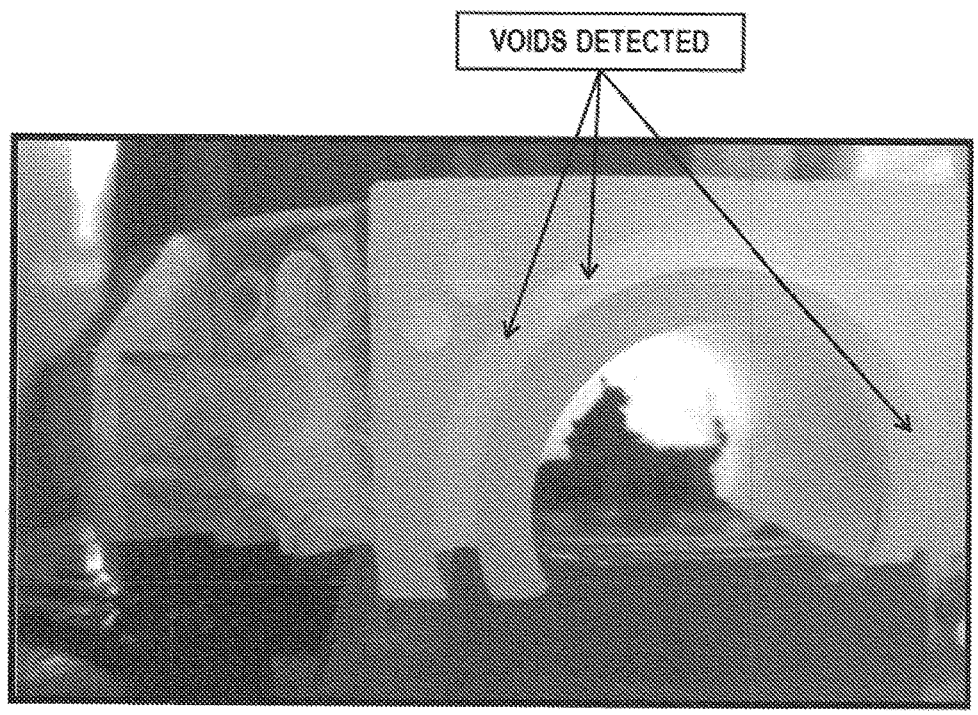

The controller provides a graphical user interface with up to five preset filters which are user selectable for image contrast enhancement. An example of the graphical user output on the laptop computer is shown in FIG. 3. The controller may be a standard laptop, with a laptop controller or lightweight tablet controller powered either by AC or remote battery, making the system truly portable. The HDMI cable is a standard interface needed for sensor power.

Defect Detection

In FIG. 1, a casting 20 is shown having a subsurface defect 22. This defect is detected by heating the casting 20, in one embodiment, as illustrated at 24 to a temperature of 100° F. This creates a thermal gradient in the casting, which affects the defect differently from the surrounding casting material. This heating and cool down control is illustrated at 26 such that when a casting 20 is heated above ambient temperature, the heat source is removed from the casting, and the casting is allowed to cool to ambient room temperature as illustrated at 28. Thereafter an infrared image 30 on a computer display 12 is viewed during the current cooling process, as illustrated at 30, with the difference in absorption at the defect as opposed to the surrounding metal accentuating the defect and indicating the presence thereof to provide defect detection, as illustrated at 32.

Figure 2:
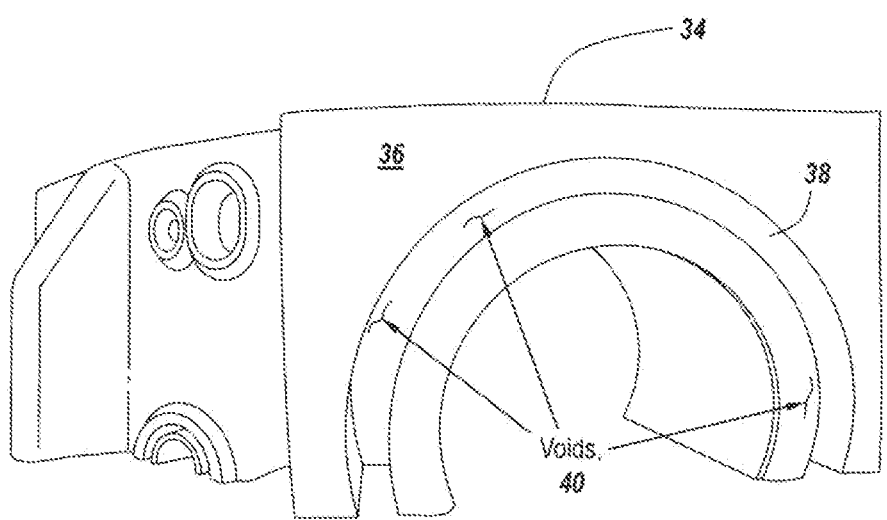
FIG. 2 is a diagrammatic representation of a metal casting in which defects are detected in the periphery of a circumferential channel in a transmission housing showing the high visibility of defects when the casting is subjected to a thermal gradient and the surface is imaged by the infrared camera of FIG. 1; and, FIG. 3 is a photograph of the metal casting of FIG. 2 illustrating the accentuation of the defects in the resulting IR image.

FIG. 2 is a diagrammatic representation of a metal casting in which defects are detected in the periphery of a circumferential channel in a transmission housing showing the high visibility of defects when the casting is subjected to a thermal gradient and the surface is imaged by the infrared camera of FIG. 1. In one embodiment, and referring now to FIG. 2, a casting for a transmission 34 has a surface 36 that contains a circumferential notch 38. Within the circumferential notch are voids 40, the presence of which is accentuated by performing the process described in FIG. 1. These subsurface voids are readily viewable due to the difference in the IR image such that even a novice can look at the computer screen and determine that there are defects in the casting.

As will be described, there are a number of technological improvements involving filtering and infrared camera manufacture which led to the high-resolution infrared camera described above.

Post Processing

The captured raw IR data is post processed in accordance with the system described in U.S. patent application 61/961,745 with various suitable image processing algorithms to produce a number of LWIR movies as well as still images. In one embodiment, five preset filters are provided, which are user selectable. The filters can be used individually or in combination and supply processed data in near real time, in one embodiment within 0.1 seconds. These image filters are available to the user via the controller user interface. The logic and description of the methods behind each preset filter is further described in U.S. Application 61/961,745; filed Oct. 21, 2013 entitled "Medical Thermal Image Processing for Vein Detection", the contents of which are incorporated herein by reference.

To demonstrate the utility of the various image processing techniques in combination, the following example is presented.

Casting Inspection Example

FIG. 3 is a photograph of the metal casting of FIG. 2 illustrating the accentuation of the defects in the resulting IR image. Referring to FIG. 3, the image demonstrates the presence of casting voids or air pockets. This was confirmed by previous methods of X ray inspection as a cross check of the results. The technique was implemented by heating up the casting to at least 100° F. to initiate a temperature gradient. The heat source was removed and the casting was allowed to cool at room temperature. The temperature profile was quickly detected using the system described in FIG. 1. Casting defects were immediately obvious and carry none of the deficiencies previously discussed.

The procedure is unrestricted and relates to any type of metallic materials. The procedure is a clean, no mess procedure and can be used for painted castings. Moreover, interpretation of test results requires minimal skill and the procedure does not require ventilation. Additionally, there are no safety hazards emanating from the device. Moreover, the process is performed at modest cost, is fast, is nondirectional and is one in which the depth of discontinuity is determined by imaging in two orthogonal directions.

As to the types of defects detectable by the subject system, first and foremost are casting voids. Moreover, air pockets are also detectable as well as shell particles. Also, any type of foreign unwanted material is detectable. Further, results are obtained in less than 0.1 seconds, making the system, a real-time system. Finally, subsurface fissures or cracks become accentuated and are easily detected.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended Claims.

What is claimed is:

1. A system for high definition thermal imaging for industrial inspection applications, said system comprising:
   a single channel, uncooled thermal sensor in a camera, wherein the sensor has low noise characteristics;
   a cable connected to the camera, wherein the cable provides power to the camera and image data from the camera;
   a controller with enhanced real time image processing software connected to the camera through the cable for processing the image data from the camera;
   wherein the enhanced real time image processing software includes a plurality of preset filters that are user selectable;
   wherein the preset filters include a spatial band-pass filter and a scene based noise suppression system for removing low frequency spatial noise and high frequency spatial noise; and
   a unit under test that is subjected to a thermal gradient, wherein the camera produces at least one thermal gradient image of a subsurface of the unit under test, wherein the thermal gradient represents temperatures at least one of above or below ambient and the image is used to inspect the unit under test, and wherein the system operates at a working distance of less than about two feet.

2. The system of claim 1, wherein the enhanced real time image processing software provides near real time image processing and an imperceptible amount of delay in the displayed image, wherein the imperceptible amount of delay is less than 0.1 seconds.

3. The system of claim 1 wherein the sensor is a 12 micron uncooled thermal sensor.

4. The system of claim 1, wherein the sensor has less than 17 micron pixel spacing.

5. The system of claim 1, wherein the camera has an objective lens and employs a manual focus adjustment for the objective lens.

6. The system of claim 1, wherein the camera is devoid of autofocus components.

7. The system of claim 1, wherein the image processing identifies subsurface defects in the unit under test.

8. The system of claim 7, wherein the subsurface defects are displayed on a display screen.

9. The system of claim 1, further comprising a graphical user interface of the controller for image contrast enhancement.

10. The system of claim 1, wherein the cable is an HDMI cable.

11. The system of claim 1, wherein the system has an increased depth of field of greater than six inches.

* * * * *